United States Patent

Plant Pat. 3,879
Patented May 4, 1976

3,879
XYLOSMA PLANT

Folke S. Olsson, Laguna Niguel, Calif.
(2154 Peck Road, Monrovia, Calif. 91016)

Filed July 26, 1974, Ser. No. 492,239
Int. Cl. A01h *5/00*
U.S. Cl. Plt.—54 1 Claim

ABSTRACT OF THE DISCLOSURE

A new and distinct variety of the Xylosma genus characterized by its hardy and compact growth and by the red edges of its juvenile leaves.

The present invention relates to a new and distinct variety of ornamental plant of the Xylosma genus.

The plant was discovered by me in 1962 as a chance seedling growing on my property at 2154 Peck Road, Monrovia, Calif. The seed parent of the new variety is an unpatented variety of *Xylosma* congestum, commonly referred to as *Xylosma senticosa,* which is widely grown in Southern California.

The new variety has been asexually reproduced by me on my property in Monrovia, Calif. by means of cuttings. A large number of plants of the new distinct variety have been reproduced by this method and in all cases the resulting plants have exhibited the distinguishing characteristics of the parent plant, indicating that the new variety is established. The new variety does not produce true from seed.

The new variety is characterized by its vigorous compact growth and by the redness of the edges of the juvenile leaves. The leaves of the new variety are small with sharply serrated margins and the shape of the leaf is elliptic to lanceolate.

The new variety differs from its seed parent *Xylosma* congestum in the smaller size of its leaves, its hardier and more compact grown and the more distinct redness of the edges of the juvenile leaves.

Figure 1:
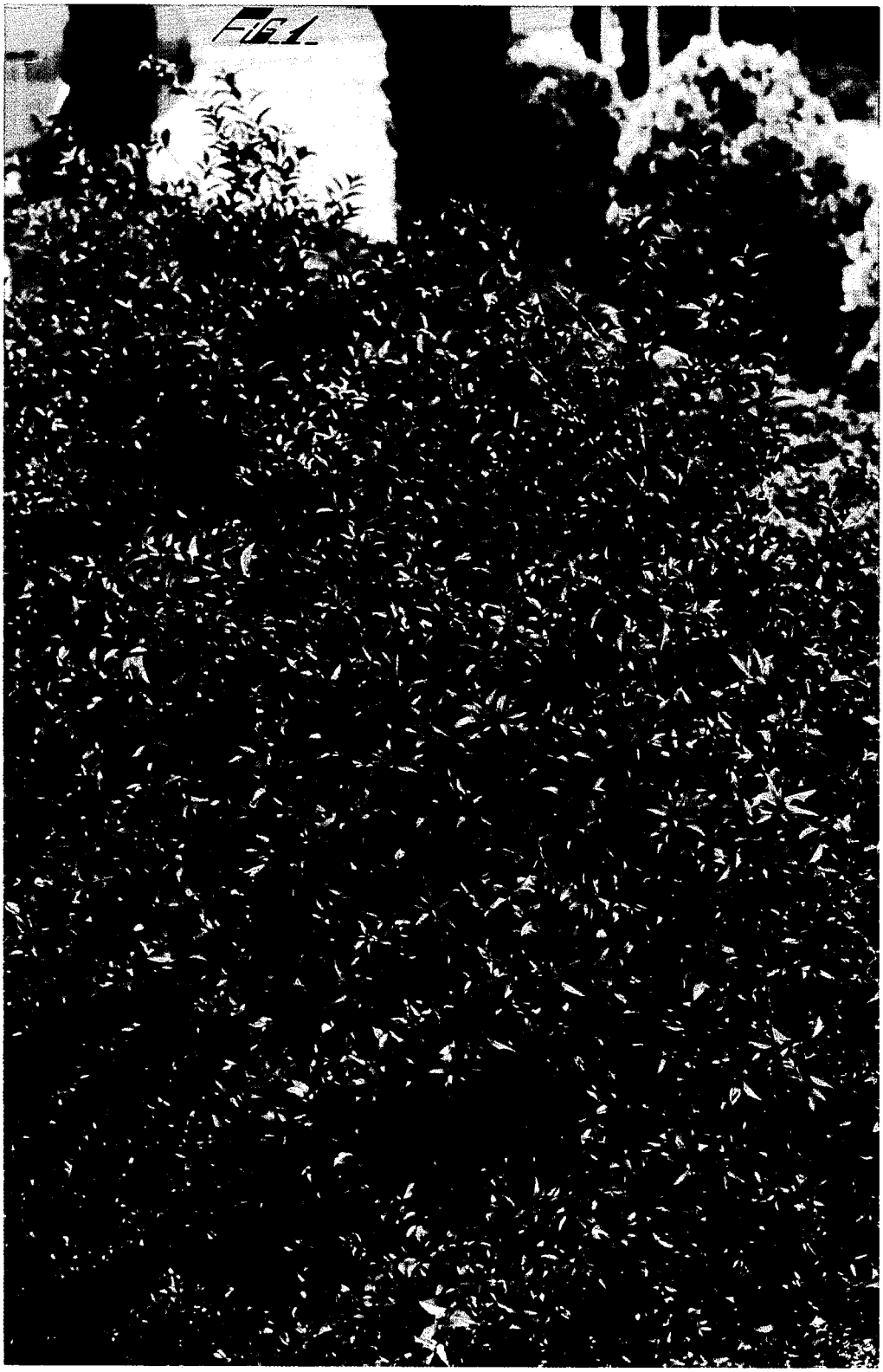
Figure 2:
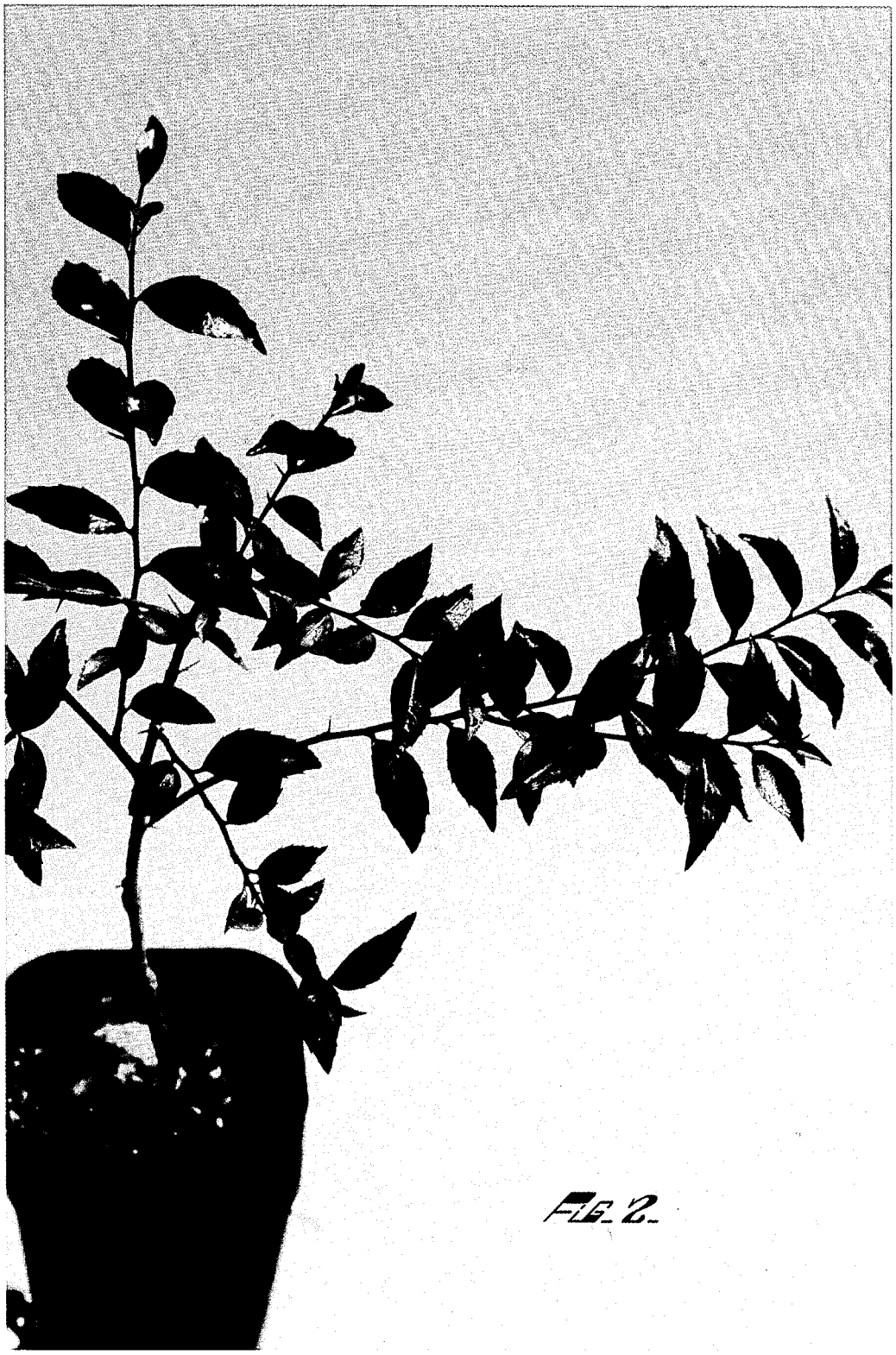
Figure 3:
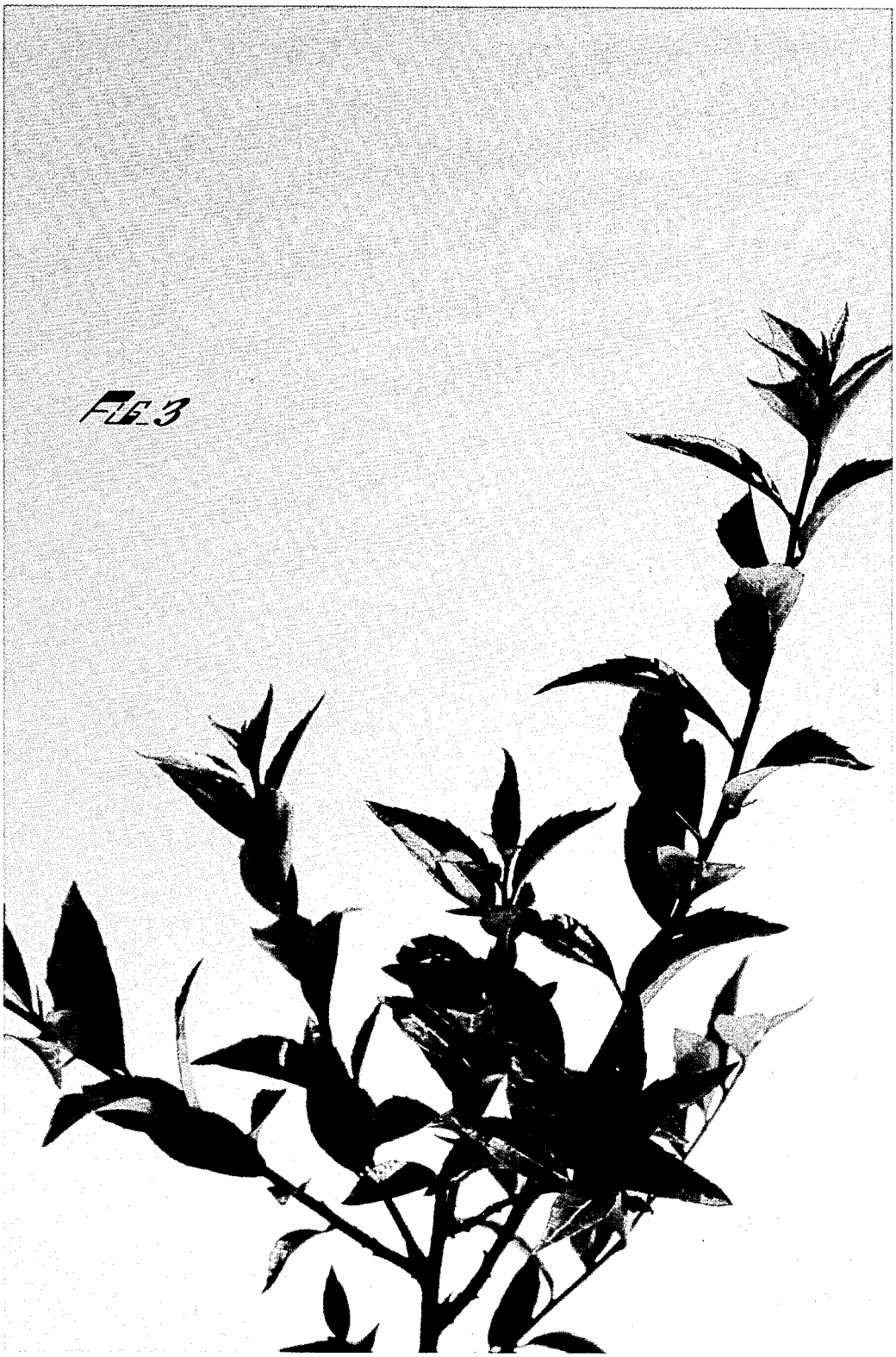

Other distinctive characteristics of the new variety are exemplified in the accompanying illustrations. FIG. 1 shows an adult plant which grew from a cutting from the original seedling. FIG. 2 shows a young plant and FIG. 3 is a close up of the leaves of a young plant. The color of the leaves is as close as can be reproduced by this method of illustration. To facilitate the identification of the important colors, the terminology adapted by the British Horticultural Colour Charts has been adopted.

The following is a brief description in some detail of the new variety.

THE PLANT

Type: Evergreen shrub or bush.

Size: The bush reaches a height of approximately four feet and a width of three feet or more. The species reaches a height of approximately twelve to eighteen feet when grown under the same conditions.

Foliage:

- Quantity.—Abundant.
- Shape.—Elliptic to lanceolate. The tip of the leaf is acute with the base of the leaf also being generally acute.
- Size.—Mature leaves are from one and one-half to two inches in length and vary in width from three-quarters to seven-eighths of an inch. The leaves of the species are approximately twice as long and wide as those of the instant variety.
- Color.—The upper portion of the leaf is Parsley Green 00962/2 and the underneath side of the leaf is Willow Green 00862/1. The margin of the leaves is Ox Blood Red 00823/3.
- New Foliage.—New growth has a dull reddish or bronzy color, subsequently changing to the green of the mature leaves.
- Margin.—The leaves have a serrate margin from the base to the tip thereof.
- Texture.—Leaves are smooth an shiny.
- Petiole.—The petiole is usually three-eighths of an inch in length when fully developed.
- Arrangement.—The leaves are alternate on the stem.

Stem: Plant develops an angular main stem that takes its time zig zagging upward. Side branches grow long and gracefully arch or droop, sometimes lying on the ground. Spines extend from the branches approximately one-quarter of an inch.

- Color.—New stem growth is Garnet Brown 00918/3 and old growth in Carnation Green 0058/2.

Flower: Flowers are insignificant and rarely seen.

The above described new variety of the Xylosma genus is a very versatile, all-foliage landscaping structure plant. It is adaptable to most soils, heat tolerant and established plants survive with little water. The height of the new variety is easily controlled and the leaves are clean and attractive. The growth is more compact than the *Xlyosma congestum* and the leaves are smaller and the reddish margins of the juvenile leaves are more distinctive than that of the *Xylosma congestum.*

I claim:

1. A new and distinct variety of the Xylosma genus as described and illustrated, characterized particularly by its hardier more compact growth, its smaller leaves, and the more distinctive margins of its juvenile leaves; all as compared with the *Xylosma senticosa.*

References Cited

Taylor's Encyclopedia of Gardening, Taylor, 1961, Houghton Mifflin Co., p. 1319 relied on.

Monrovia Nursery Co. wholesale catalog, 1971, p. 85 relied on.

ROBERT E. BAGWILL, Examiner